(12) United States Patent
Marazano et al.

(10) Patent No.: US 6,232,319 B1
(45) Date of Patent: May 15, 2001

(54) SUBSTITUTED TETRAHYDROPYRIDIN DERIVATIVES, METHOD OF PREPARATION AND PHARMACEUTICAL COMPOSITIONS CONTAINING THEM

(75) Inventors: Christian Marazano, Fontenay aux Roses; Delphine Compere, Paris; Bhupesh Chandra Das, Gif sur Yvette; Jean Lepagnol, Chaudon, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/319,341

(22) PCT Filed: Dec. 2, 1997

(86) PCT No.: PCT/FR97/02172

§ 371 Date: Jun. 4, 1999

§ 102(e) Date: Jun. 4, 1999

(87) PCT Pub. No.: WO98/24765

PCT Pub. Date: Jun. 11, 1998

(30) Foreign Application Priority Data

Dec. 5, 1996 (FR) .................................................. 96 14951

(51) Int. Cl.$^7$ ....................... A61K 31/435; C07D 211/70
(52) U.S. Cl. ...................... 514/277; 546/339; 546/340; 546/283.7
(58) Field of Search ..................................... 546/339, 340; 514/277

(56) References Cited

PUBLICATIONS

Database on Caplus, AN: 2000:796106, Jones et al.*
Driessens, Frank et al.; "Sedum Alkaloids. XI. Synthesis of sedinone and sedacrine by application of anodic oxidation"; Can. J. Chem. (1991), 62(2), 211–17.

H.E.J. Res: "Andrachine, an alkaloid from *Andrachne aspera*"; Phytochemistry, vol. 276, No. 2, 1987.

Williams, H. et al.; ".delta.–3–piperidine alkaloids from the toxic plant *Lobelia berlandieri*"; J. Agric. Food Chem., vol. 35, No. 1, 1987, pp 19–22.

Chemical Abstracts, vol. 105, No. 5, Aug. 4, 1986; Columbus, Ohio, U.S.; Abstract No. 43121; Natsume, Mitsutaka: "Synthesis of alkaloids containing piperidine ring".

Yuki Gosei Kagaku Kyokaishi (1986), 44(4), 326–39.

Bailey, Thomas R. et al.: "Total synthesis of anhydrocannabisativene"; J. Am. Chem. Soc. (1984), 106(11), 3240–5.

Colau, B.; Hootele, C.: Sedum alkaloids: Can. J. Chem.; vol. 61, No. 3, 1983, pp 470–472.

* cited by examiner

*Primary Examiner*—Jane Fan
(74) *Attorney, Agent, or Firm*—The Firm of Hueschen and Sage; G. Patrick Sage

(57) ABSTRACT

The invention relates to compounds of general formula (I):

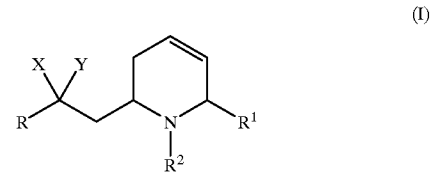

(I)

in which R, $R^1$, $R^2$, X and Y are as defined in the description, their geometrical and/or optical isomers, and their addition salts with a pharmaceutically-acceptable acid or base, as well as to medicaments containing the same.

6 Claims, No Drawings

SUBSTITUTED TETRAHYDROPYRIDIN DERIVATIVES, METHOD OF PREPARATION AND PHARMACEUTICAL COMPOSITIONS CONTAINING THEM

The present application is a U.S. National Application filed under 35 USC 371 of PCT/FR97/02172, filed Dec. 2, 1997 based upon French application Ser. No. 96/14,951 filed Dec. 5, 1996.

The present invention relates to new substituted tetrahydropyridine derivatives, to a process for preparing them and to pharmaceutical compositions containing them.

Many studies in the literature describe the synthesis of compounds derived from lobeline as alkaloids capable of interacting with nicotinic receptors. There may be mentioned especially Hootelé for the synthesis of sedinone and sedacrine (Hootelé C., Driessens F., Can. J. Chem., 1991, 69 (2), pp. 211–17) and Natsume for the synthesis of sedinine (Natsume M., Ogawa M., Hétérocyles [sic], 1985, 23 (4), pp. 831–4).

The compounds of the present invention are new and especially advantageous from a pharmacological standpoint for their specific interaction with nicotinic receptors, finding their application in the treatment of diseases associated with cerebral aging.

The aging of the population through an increase in life expectancy has given rise to a concomitant large increase in the incidence of neurodegenerative diseases associated with age, and in particular Alzheimer's disease. The main clinical manifestations of cerebral aging, and most particularly of neurodegenerative diseases, are the defects of mnestic and cognitive functions which can lead to dementia. It is widely demonstrated that, among the different neurotransmitters, acetylcholine has a preponderant place in memory functions, and that the cholinergic neuronal pathways are dramatically destroyed in certain neurodegenerative diseases or where there is a defect of activation during cerebral aging. Accordingly, numerous therapeutic approaches have been directed towards preventing destruction of the neuromediator via acetylcholinesterase or have sought to substitute themselves for the deficient neuromediator. In the latter case, the cholinergic agonists proposed have been of the muscarinic type, specific for the M1 postsynaptic receptors.

Recently, it has been shown that, in fact, the cholinergic impairment associated with Alzheimer's disease affected the neurons bearing the nicotinic receptors (N) more than those bearing the muscarinic receptors (Schroder et al., in "Alzheimer disease: therapeutic strategies", ed. Birkhauser Boston, 1994, 181–185). Furthermore, numerous studies have shown that nicotine possesses memory-facilitating properties (Warburton, Prog. Neuropsychopharmacol, 1992, 16, 181–191) and that these properties exert their effect just as much on the mnestic functions (Levin and Torry, Psychopharmacol., 1996, 123, 88–97) as on the faculties of attention and of vigilance (Turchi et al., Psychopharmacol., 1995, 118, 195–205). Moreover, nicotine exerts neuroprotective effects with respect to excito-toxic agents such as glutamate (Akaike et al., Brain Res., 1994, 644, 181–187). These collective data are very probably to be linked to the epidemiological studies which have shown a lower incidence of Alzheimer's or Parkinson's disease among smokers.

Although the nicotinic receptors are not yet fully classified, it is nowadays well demonstrated that these receptors can be different in nature and, jointly, can have very diverse electrophysiological properties (for a review: Williams et al., Drug News Perspect., 1994, 7, 205–223). Accordingly, nicotine possesses both beneficial promnestic properties demonstrated in Alzheimer's patients (Wilson et al., 1995, 51, 509–514) and deleterious properties of habituation by activation of receptors having variable kinetics of inactivation.

Independently of nicotine itself, other nicotinic agonists have been described, including lobeline which possesses potent promnestic properties (Decker et al., Pharmacol. Biochem. Behav., 45, 571–576) but, contrary to nicotine, which binds preferentially to certain rapidly desensitizing receptor subtypes, designated α7 (Marks et al., J. Pharmacol. Exp. Ther., 1986, 30, 427–436). Accordingly, lobeline is potentially without addictive potential.

The compounds of the present invention were hence synthesized as nicotinic ligands possessing promnestic properties for the treatment of memory defects associated with cerebral aging and with neurodegenerative diseases such as Alzheimer's disease, Parkinson's disease, Pick's disease, Korsakoff's disease and frontal and subcortical dementias.

More specifically, the present invention relates to the compounds of formula (I):

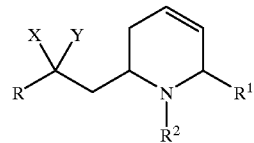

(I)

in which:
X represents a hydrogen atom,
Y represents a hydroxyl group,
or X and Y together form an oxo group,
R represents a linear or branched ($C_1$–$C_6$) alkyl group or a phenyl group optionally substituted with one or more halogen atoms or one or more linear or branched ($C_1$–$C_6$) alkyl, ($C_1$–$C_6$) alkoxy, linear or branched ($C_1$–$C_6$) polyhaloalkyl or hydroxyl groups,
$R^1$ represents a hydrogen atom or a group of formula (II):

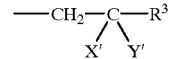

(II)

in which:
X' represents a hydrogen atom,
Y' represents a hydroxyl group,
or X' and Y' simultaneously represent a linear or branched ($C_1$–$C_6$) alkoxy group,
or X' and Y' together form an oxo group or a linear or branched ($C_1$–$C_4$) alkylenedioxy group,
$R^3$ represents a linear or branched ($C_1$–$C_6$) alkoxy group or a phenyl group optionally substituted with one or more halogen atoms or one or more linear or branched ($C_1$–$C_6$) alkyl, ($C_1$–$C_6$) alkoxy, linear or branched ($C_1$–$C_6$) polyhaloalkyl or hydroxyl groups,
$R^2$ represents a hydrogen atom or a linear or branched ($C_1$–$C_6$) alkyl group optionally substituted with one or more, identical or different, optionally substituted aryl, linear or branched ($C_1$–$C_6$) alkoxy or hydroxyl groups,
on the understanding that, when R and $R^2$ simultaneously represent a methyl group, X represents a hydrogen atom, Y represents a hydroxyl group and $R^1$ represents a group of formula (II) in which X' represents a hydrogen atom and Y' a hydroxyl group, then $R^3$ cannot represent a phenyl group, their isomers as well as their addition salts with a pharmaceutically acceptable acid or base.

Optionally substituted aryl is understood to mean phenyl or naphthyl, each of these groups being optionally substituted with one or more halogen atoms or one or more linear or branched ($C_1$–$C_6$) alkyl, ($C_1$–$C_6$) alkoxy, linear or branched ($C_1$–$C_6$) polyhaloalkyl or hydroxyl groups.

Among pharmaceutically acceptable acids, there may be mentioned, without implied limitation, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic, camphoric, and the like, acids.

Among pharmaceutically acceptable bases, there may be mentioned, without implied limitation, sodium hydroxide, potassium hydroxide, triethylamine, tert-butylamine, and the like.

The present invention relates preferentially to the compounds of formula (I) in which X represents a hydrogen atom and Y a hydroxyl group, and more especially the compounds of formula (I) in which X represents a hydrogen atom, Y a hydroxyl group and $R^1$ represents a hydrogen atom or a group of formula (II):

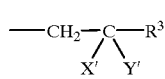
(II)

where X', Y' and $R^3$ are as defined above.

The invention also extends to the process for preparing the compounds of formula (I), wherein a compound of formula (III):

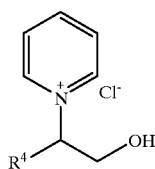
(III)

in which $R^4$ represents a linear or branched ($C_1$–$C_6$) alkyl or an aryl group, optionally substituted, is used as starting material, which is reacted with sodium borohydride in the presence of sodium hydroxide to obtain the compound of formula (IV):

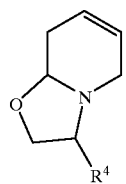
(IV)

in which $R^4$ is as defined above, which, subjected to the Reformatsky reagent $BrZnCH_2COOEt$, yields the compound of formula (V):

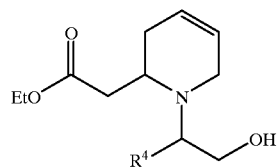
(V)

in which $R^4$ has the same definition as above, which is subjected successively to the action of dimethylthexylchlorosilane and then to that of lithium aluminum hydride to yield the compound of formula (VI):

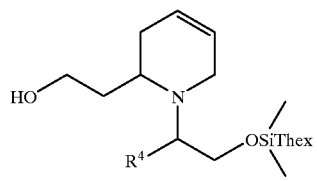
(VI)

in which $R^4$ is as defined above and Thex represents a (1,1,2)-trimethylpropyl group, which is subjected to Swern oxidation to yield the compound of formula (VII):

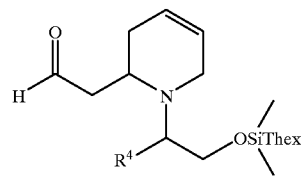
(VII)

in which $R^4$ and Thex are defined as above, which is subjected to the action of the magnesium compound RMgBr where R is as defined in the formula (I), to yield the compound of formula (VIII):

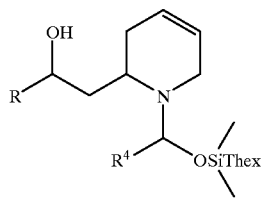
(VIII)

in which R, $R^4$ and Thex are as defined above, which is, where appropriate, subject to an oxidizing agent to yield the compound of formula (IX):

(IX)

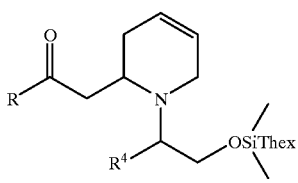

in which R, $R^4$ and Thex have the same definitions as above, the collective compounds (VIII) and (IX) forming the compound of formula (X):

(X)

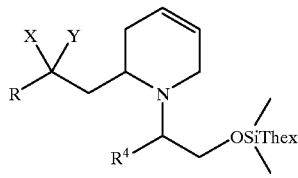

in which R, $R^4$, X, Y and Thex are as defined above, which compound of formula (X) is hydrolyzed in an acid medium to yield the compound of formula (I/a), a special case of the compounds of formula (I):

(I/a)

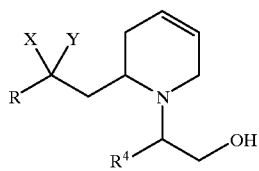

in which R, X, Y and $R^4$ are as defined above,
which is:
either treated, when X represents a hydrogen atom and Y a hydroxyl group, with hydrogen in the presence of palladium on charcoal to obtain the compound of formula (I/b), a special case of the compounds of formula (I):

(I/b)

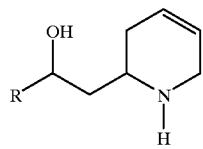

in which R is as defined above,
or treated with a diphenylalkylsulfonium tetrafluoroborate of formula (XI):

(XI)

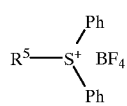

in which $R^5$ represents a linear or branched ($C_1$–$C_6$) alkyl group, to give rise to the compound of formula (XII):

(XII)

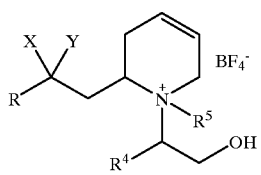

in which R, $R^4$, $R^5$, X and Y are as defined above,
which compound of formula (XII) is subjected to the action of potassium tert-butanolate in tert-butanol to yield the compound of formula (I/c), a special case of the compounds of formula (I):

(I/c)

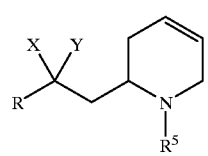

in which R, X, Y and $R^5$ are as defined above,
which is, in the case where X represents a hydrogen atom and Y a hydroxyl group, treated with metachloroperbenzoic acid to obtain the compound of formula (XIII):

(XIII)

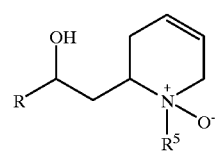

in which R and $R^5$ have the same definition as above,
which is subjected to the action of trifluoroacetic anhydride to yield the compound of formula (XIV):

(XIV)

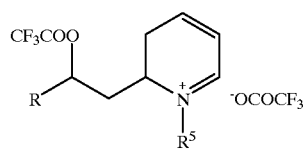

in which R and $R^5$ are as defined above,
which is treated with the Reformatsky reagent BrZnCH$_2$COOR$^6$ where $R^6$ represents a linear or branched ($C_1$–$C_6$) alkyl group, to obtain the compound of formula (I/d), a special case of the compounds of formula (I):

(I/d)

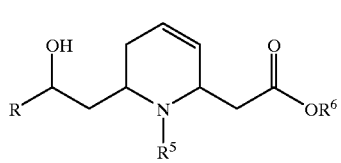

in which R, $R^5$ and $R^6$ have the same definition as above, which is subjected successively to the Weinreb reagent MeO   Cl
  \\N—Al/
  /    \\
Me     Me and then to the action of a lithium compound $R^7$-Li where $R^7$ represents a phenyl group optionally substituted with one or more halogen atoms or one or more linear or branched $(C_1-C_6)$ alkyl, $(C_1-C_6)$ alkoxy, linear or branched $(C_1-C_6)$ polyhaloalkyl or hydroxyl groups, to yield the compound of formula (I/e), a special case of the compounds of formula (I):

(I/e)

in which R, $R^5$ and $R^7$ are as defined above,
which is:
  either subjected to an oxidizing agent to yield the compound of formula (I/f), a special case of the compounds of formula (I):

(I/f)

in which R, $R^5$ and $R^7$ have the same definitions as above,
  or subjected to a reducing agent to yield the compound of formula (I/g), a special case of the compounds of formula (I):

(I/g)

in which R, $R^5$ and $R^7$ are as defined above,
  or protected in acetal form by the action of an alcohol in an acid medium, to obtain the compound of formula (I/h), a special case of the compounds of formula (I):

(I/h)

in which R, $R^5$ and $R^7$ are as defined above and X" and Y" simultaneously represent a linear or branched $(C_1-C_6)$ alkoxy group or together form a linear or branched $(C_1-C_4)$ alkylenedioxy group,
  the compounds (I/a) to (I/h) forming the collective compounds of the invention, which are purified, where appropriate, according to a standard purification technique, and which can, if so desired, be separated into their different optical isomers or salified with a pharmaceutically acceptable acid or base.

The present invention also relates to the synthesis intermediates of formula (V), (XII) and (XIII) described in the process detailed above.

The starting pyridinium salts used in the process described above are accessible to a person skilled in the art according to processes well known in the literature such as, for example, the one described by Y. Génisson, C. Marazano, M. Mehmandoust, D. Gnecco and B. C. Das, Synlett, 1992, p. 431.

The compounds of formula (I) possess advantageous pharmacological properties.

Through their memory-facilitating properties and as a result of their preferential affinity for the α7 nicotinic receptors, the compounds of the present invention are hence useful for the treatment of memory defects associated with cerebral aging and with neurodegenerative diseases such as Alzheimer's disease, Parkinson's disease, Pick's disease, Korsakoff's disease and frontal and subcortical dementias.

The subject of the present invention is also pharmaceutical compositions containing the products of formula (I), their optical isomers or one of their addition salts with a pharmaceutically acceptable base or acid, alone or in combination with one or more inert, nontoxic excipients or vehicles.

Among the pharmaceutical compositions according to the invention, there may be mentioned more especially those which are suitable for oral, parenteral, nasal, rectal, perlingual, ocular or respiratory administration, and in particular simple or sugar-coated tablets, sublingual tablets, sachets, packets, hard gelatin capsules, preparations to be dissolved under the tongue, lozenges, suppositories, creams, ointments, skin gels, preparations to be injected or to be taken by mouth, aerosols and eye or nasal drops.

The appropriate dosage varies according to the patient's age and weight, the administration route and the nature of the therapeutic indication and of any possible associated treatments, and ranges between 1 and 500 mg per day in one or several administrations.

The examples which follow illustrate the invention but in no way limit it.

EXAMPLE 1

(1S,1'S,2"S)-2-[1-(2-Hydroxy-1-phenyl-ethyl)-1,2,3, 6-tetrahydro-2-pyridyl]-1-phenylethanol Stage A: (3S,8aS)-3-Phenyl-2,3,8,8a-tetrahydro-[5H]-oxazolo[3,2-a]pyridine [sic]

42.5 mmol of (1'S)-1-(2-hydroxy-1-phenyl-ethyl) pyridinium chloride dissolved in water are added slowly to 132 mmol of sodium borohydride in solution in a two-phase system of 5 N sodium hydroxide (100 ml) and ether (400 ml) at room temperature. After one hour of vigorous magnetic stirring, the organic phase is separated after settling has taken place and filtered rapidly through a short column of alumina (60 g). After evaporation of the solvent under reduced pressure, the oxazolidine is obtained.

Orange-red oil

Stage B: (1'S,2"S)-[1-(2-Hydroxy-1-phenylethyl)-2-(ethoxycarbonylmethyl)]-1,2,3,6-tetrahydro pyridine [sic]

118.61 mmol of (3S,8aS)-3-phenyl-2,3,8,8a-tetrahydro-[5H]-oxazolo[3,2-a]pyridine [sic] dissolved in anhydrous ether (180 ml) are added dropwise to the Reformatsky reagent BrZnCH$_2$COOEt (474 ml, 474 mmol) placed at 0° C. under an argon atmosphere and with magnetic stirring. When the addition is complete, the temperature is allowed to rise to 25° C. and stirring is then maintained at this temperature overnight. The reaction mixture is poured into saturated ammonium chloride solution at 0° C. and then filtered through a Buchner funnel in order to remove insoluble precipitates. The organic phase is extracted with ether and then with ethyl acetate and lastly dried over magnesium sulfate. After evaporation of the solvent under reduced pressure, the mixture of tetrahydropyridines is obtained in the proportions 60:40, respectively (determined by gas chromatography after acetylation of the crude reaction product). The two diastereoisomers are separated by chromatography on silica gel, eluted with a gradient of 400 ml of ethyl acetate/heptane (0:100 to 50:50 in 5% increments).

Orange-yellow oil

HR (CI) (methane): $C_{17}H_{24}NO_3$

Calculated: 290.1756

Found: 290.1769

Stage C: (1'S,2"S)-(1-{2-[Dimethyl-(1,1,2-trimethyl propyl)silanyloxy]-1-phenylethyl}-2-(ethoxy carbonylmethyl})-1,2,3,6-tetrahydropyridine [sic]

30.65 mmol of (1'S,2"S)-[1-(2-hydroxy-1-phenyl-ethyl)-2-(ethoxycarbonylmethyl)]-1,2,3,6-tetrahydro-pyridine [sic] are diluted in anhydrous dichloromethane (70 ml) and then placed at 0° C. under an argon atmosphere. Dimethylthexylchlorosilane (1.5 eq, 9.0 ml, 45.98 mmol) is added, followed by triethylamine (2.5 eq, 10.8 ml, 76.64 mmol) as well as a catalytic amount of dimethylaminopyridine. The temperature is allowed to rise to 25° C. and stirring is maintained at this temperature overnight. The reaction mixture is poured into saturated ammonium chloride solution at 0° C. The organic phase is extracted with dichloromethane and then dried over magnesium sulfate. After evaporation of the solvent under reduced pressure, the crude reaction product is filtered through a short column of alumina (140 g), eluted with an ethyl acetate/heptane gradient (0:100 to 30:70 in 10% increments). The silylated monoalkyl derivative is thus isolated.

Yellow oil $[\alpha]_D$: +24 (c=1.7, CHCl$_3$)

Stage D: (1'S,2"S)-2-(1-{2-[Dimethyl-(1,1,2-trimethyl propyl)silanyloxy]-1-phenylethyl}-1,2,3,6-tetrahydro-2-pyridyl)ethanol 27.45 mmol of (1'S,2"S)-(1-{2-[dimethyl-(1,1,2-trimethylpropyl)silanyloxy]-1-phenylethyl}-2-ethoxycarbonylmethyl)-1,2,3,6-tetrahydropyridine [sic] are diluted in anhydrous THF (90 ml) and placed at 0° C. with magnetic stirring. Lithium aluminum hydride (1.5 eq, 2.56 g, 41.17 mmol) is added slowly. The temperature is allowed to rise to 25° C. and the mixture is left stirring overnight. When reaction is complete, ethyl acetate is added, followed by a few drops of water to destroy the excess hydride. The solution obtained is filtered through Celite, rinsed with ethyl acetate and then with methanol. The filtrate is dried over magnesium sulfate and evaporated under reduced pressure. The crude reaction product is then purified by filtration through a short column of alumina (110 g), eluted with an ethyl acetate/heptane gradient (0:100 to 20:80 in 5% increments). The reduced silylated monoalkyl is thus isolated.

Pale yellow oil

HR (CI) (methane): $C_{23}H_{40}NO_2Si$

Calculated: 390.2828

Found: 390.2803

$[\alpha]_D$: −11 (c=0.65, CHCl$_3$)

Stage E: (1'S,2"S)-2-(1-{2-[Dimethyl-(1,1,2-trimethyl propyl)silanyloxy]-1-phenylethyl}-1,2,3,6-tetrahydro-2-pyridyl)ethanal Oxalyl chloride (4 eq, 8.40 ml, 97.56 mmol) in solution in anhydrous dichloromethane (180 ml) is cooled to −78° C. Dimethyl sulfoxide (6 eq, 10.40 ml, 146.34 mmol) diluted with anhydrous dichloromethane (180 ml) is added with stirring and under an argon atmosphere. After 10 minutes, 24.39 mmol of (1'S,2"S)-2-(1-{2-dimethyl-(1,1,2-trimethylpropyl)silanyloxy]-1-phenylethyl}-1,2,3,6-tetrahydro-2-pyridyl)ethanol diluted in anhydrous dichloromethane (30 ml) are added dropwise. Magnetic stirring is maintained at −78° C. for 15 minutes. Triethylamine (8 eq, 27.5 ml, 195.12 mmol) is then added and the reaction mixture is then allowed to return to room temperature. After the addition of water, the organic phase is extracted with dichloromethane, dried over magnesium sulfate and evaporated under reduced pressure. The aldehyde obtained is reacted directly in view of its instability.

Stage F: (1'S,2"S)-2-(1-{2-[Dimethyl-(1,1,2-trimethyl propyl)silanyloxy]-1-phenylethyl}-1,2,3,6-tetrahydro-2-pyridyl)-1-phenylethanol Phenylmagnesium bromide (1.5 eq, 61 ml, 36.59 mmol) is poured into a three-necked flask under an argon atmosphere and with magnetic stirring at 0° C. The crude product of the Swern reaction (9.44 g, 24.39 mmol) diluted in anhydrous ether (80 ml) is added dropwise by means of a dropping funnel. When the addition is complete, the temperature is allowed to rise to 25° C. and stirring is maintained at this temperature overnight. The reaction mixture is then poured into saturated ammonium chloride solution at 0° C. The organic phase is extracted with ether and then with dichloromethane and lastly dried over magnesium sulfate. After evaporation of the solvent under reduced pressure, the mixture of alcohols is obtained in the proportions 60:40, respectively (determined by integration of the protons in NMR). The two diastereoisomers are separated by chromatography on alumina (360 g), eluted with a gradient of 400 ml of ethyl acetate/heptane (0:100 to 5:95 in 1% increments, then 5:95 to 20:80 in 5% increments). The preponderant diastereoisomer is isolated.

Brown paste

HR (CI) (methane): $C_{29}H_{44}NO_2Si$

Calculated: 466.3141

Found: 466.3152

$[\alpha]_D$: −18 (c=0.22, CHCl$_3$)

Stage G: (1S,1'S,2"S)-2-[1-(2-Hydroxy-1-phenylethyl)-1,2,3,6-tetrahydro-2-pyridyl]-1-phenylethanol 9.81 mmol of (1'S,2"S)-2-(1-{2-[dimethyl-(1,1,2-trimethylpropyl)silanyloxy]-1-phenylethyl}-1,2,3,6-tetrahydro-2-pyridyl)-1-phenylethanol are diluted in a hydrochloric acid/water/tetrahydrofuran mixture in the proportions 3:1:1. The resulting mixture is left overnight with magnetic stirring at room temperature. The reaction medium is then extracted, in the presence of potassium carbonate, with ether and then with dichloromethane. The organic phase is dried over magnesium sulfate and evaporated under reduced pressure. The crude reaction product is then filtered through a short column of alumina (95 g) eluted with an ethyl acetate/heptane gradient (0:100 to 100:0 in 10% increments) followed by a methanol/dichloromethane gradient (0:100 to 5:95 in 1% increments). The diol is thus isolated.

Yellow oil

HR (CI) (methane): $C_{21}H_{26}NO_2$

Calculated: 324.1964

Found: 324.1965

$[\alpha]_D$: −49 (c=1.1, $CHCl_3$)

EXAMPLE 2

(1R,1'S,2"S)-2-[1-(2-Hydroxy-1-phenyl ethyl)-1,2,3,6-tetrahydro-2-pyridyl]-1-phenylethanol The same process is used as for Example 1, choosing the less abundant diastereoisomer in Stage F.

Yellow oil

HR (CI) (methane): $C_{21}H_{26}NO_2$

Calculated: 324.1963

Found: 324.1941

$[\alpha]_D$: +52 (c=2.4, $CHCl_3$)

Examples 3 to 6 are obtained using the same process as for Example 1, selecting the appropriate magnesium compound in Stage F.

EXAMPLE 3

(1R,1'S,2"S)-1-[1-(2-Hydroxy-1-phenyl ethyl)-1,2,3,6-tetrahydro-2-pyridyl]-2-propanol

EXAMPLE 4

(1R,1'S,2"S)-1-[1-(2-Hydroxy-1-phenyl ethyl)-1,2,3,6-tetrahydro-2-pyridyl]-4-methyl-2-pentanol

EXAMPLE 5

(1S,1'S,2"S)-2-[1-(2-Hydroxy-1-phenyl ethyl)-1,2,3,6-tetrahydro-2-pyridyl]-1-(4-methylphenyl)ethanol

EXAMPLE 6

(1S,1'S,2"S)-2-[1-(2-Hydroxy-1-phenyl ethyl)-1,2,3,6-tetrahydro-2-pyridyl]-1-(3-trifluoromethylphenyl)ethanol

EXAMPLE 7

(1S,2"S)-2-(1-Methyl-1,2,3,6-tetrahydro-2-pyridyl)-1-phenylethanol

Stage A: (1S,2"S)-2-[1-Methyl-1-(2-hydroxy-1-phenyl ethyl)-1,2,3,6-tetrahydro-2-pyridiniumyl]-1-phenylethanol tetrafluoroborate 15.3 mmol of the compound of Example 1 are dissolved in distilled acetonitrile (160 ml). Diphenylmethylsulfonium tetrafluoroborate (1.1 eq, 6.67 g, 21.09 mmol) is added with magnetic stirring and the mixture is brought to reflux for 48 hours. After evaporation of the solvent under reduced pressure, the crude reaction product is chromatographed on alumina (195 g), eluted with a gradient of 200 ml of ethyl acetate/heptane (0:100 to 50:50 in 10% increments) in order to remove the diphenyl sulfide and the unreacted product, and then with a gradient of 100 ml of methanol/dichloromethane (0:100 to 5:95 in 0.5% increments, followed by 5:95 to 50:50 in 5% increments). The methylated product is thus isolated.

Light beige foam

Stage B: (1S,2"S)-(1-Methyl-1,2,3,6-tetrahydro-2-pyridyl)-1-phenylethanol [sic]

3.56 mmol of the salt obtained in Stage A are dissolved in distilled tert-butanol (40 ml). Potassium tert-butanolate (1.5 eq, 600 mg, 5.34 mmol), previously sublimed (145° C., P=0.6 mmHg), is added. The mixture is brought to reflux for 2 hours. The cooled reaction mixture is poured into saturated ammonium chloride solution, extracted with dichloromethane and dried over magnesium sulfate. The manipulation is repeated in this way 3 times. After evaporation of the solvent under reduced pressure, the crude product is chromatographed on alumina (70 g), eluted with an ethyl acetate/heptane gradient (0:100 to 50:50 in 10% increments) followed by a methanol/dichloromethane gradient (0:100 to 6:94 in 0.5% increments).

Orange-yellow oil

HR (EI): $C_{14}H_{19}NO$

Calculated: 217.1467

Found: 217.1464

EXAMPLE 8

(1R,2"S)-2-(1-Methyl-1,2,3,6-tetrahydro-2-pyridyl)-1-phenylethanol

The procedure is as for Example 7, starting from the compound of Example 2.

Orange-yellow oil

HR (EI): $C_{14}H_{19}NO$

Calculated: 217.1467

Found: 217.1466

EXAMPLE 9

(2"S)-2-Benzoylmethyl-1-methyl-1,2,3,6-tetrahydropyridine

The procedure is as in Stage E of Example 1, starting from the compound of Example 7 or 8.

EXAMPLE 10

(1R,2"S)-1-[1-Methyl-1,2,3,6-tetrahydro-2-pyridyl]-2-propanol

The procedure is as for Example 7, starting from the compound of Example 3.

EXAMPLE 11

(1S,2"S)-2-[1-Methyl-1,2,3,6-tetrahydro-2-pyridyl]-1-(4-methylphenyl)ethanol

The procedure is as for Example 7, starting from the compound of Example 5.

EXAMPLE 12

(2"S)-2-(4-Methylbenzoylmethyl)-1-methyl-1,2,3,6-tetrahydropyridine

The procedure is as in Stage E of Example 1, starting from the compound of Example 11.

EXAMPLE 13

(1S,2"S)-2-(1-Methyl-6-ethoxycarbonyl-methyl-1,2,3,6-tetrahydro-2-pyridyl)-1-phenylethanol Stage A: (1S,2"S)-2-(1-Methyl-1,2,3,6-tetrahydro-2-pyridyl)-1-phenylethanol N-oxide 1 mmol of the compound of Example 7 is diluted in anhydrous dichloromethane (10 ml) and placed at 0° C. with magnetic stirring. Meta-chloroperbenzoic acid (1.5 eq, 371 mg, 1.5 mmol) is added. After 15 minutes, the mixture is rapidly filtered through a short column of alumina (60 times the theoretical weight), eluted with a methanol/dichloromethane gradient (0:100 to 5:95 in 1% increments). After evaporation of the solvent under reduced pressure, the N-oxide is isolated and used immediately in the next stage of the reaction.

Stage B: (1S,2"S)-2-(1-Methyl-2,3-dihydro-2-pyridinium yl)-1-phenylethane trifluoroacetate 1 mmol of the N-oxide obtained in Stage A is taken up with anhydrous dichloromethane (10 ml) and the medium is placed at 0° C. Trifluoroacetic anhydride (2.5 eq, 0.35 ml, 2.5 mmol) is added slowly. The reaction is left for 20 to 30 minutes at 0° C. The solvent and the excess reagent are evaporated off under reduced pressure to yield the dihydropyridinium salt. In view of its instability, the compound is alkylated directly.

Stage C: (1S,2"S)-2-(1-Methyl-6-ethoxycarbonylmethyl-1,2,3,6-tetrahydro-2-pyridyl)-1-phenylethanol The dihydropyridinium salt obtained in Stage B is diluted with anhydrous dichloromethane (10 ml) and added dropwise to a 1 molar solution of Reformatsky reagent (5 eq, 5 ml, 5 mmol) placed at 0° C. under an argon atmosphere and with magnetic stirring. When the addition is complete, the temperature is allowed to rise to 25° C. and stirring is maintained at this temperature overnight. The reaction mixture is poured into a saturated ammonium chloride solution at 0° C. The organic phase is extracted with dichloromethane and then dried over magnesium sulfate. After evaporation of the solvent under reduced pressure, the crude reaction product is filtered through a very short column of alumina, eluted with an ethyl acetate/heptane (50:50) mixture. An inseparable mixture of diastereoisomers (182 mg, 0.60 mmol) in the proportions 60:40 (determined by integration of the protons in NMR) is then obtained.

Yellow oil

MS (CI) (isobutane): m/z 360 ([M+57]$^+$, 7), 304 ([M+H]$^+$, 100), 216 ([M—CH$_2$COOCH$_2$CH$_3$]$^+$, 8)

EXAMPLE 14

(1R,2"S)-1-(1-Methyl-6-ethoxycarbonyl-methyl-1,2,3,6-tetrahydro-2-pyridyl)-2-propanol The procedure is as in Example 13, starting from the compound of Example 10.

EXAMPLE 15

(1S,2"S)-2-(1-Methyl-6-benzoylmethyl-1,2,3,6-tetrahydro-2-pyridyl)-1-phenyl ethanol Stage A: (1S,2"S)-2-[6-(2-Hydroxy-2-phenylethyl)-1-methyl-1,2,5,6-tetrahydro-2-pyridyl]-N-methoxy-N-methylacetamide N,O-Dimethylhydroxylamine chloride [sic] (3 eq, 88 mg, 0.90 mmol) diluted with anhydrous toluene (1.8 ml) is placed at 0–5° C. under argon and with stirring. Trimethylaluminum, 2 M commercial solution in toluene (1.15 eq, 0.52 ml, 1.04 mmol) is added dropwise. When the addition is complete, the bath of ice-cold water is removed and the mixture is left stirring for 2 hours. The Weinreb reagent thus prepared is added dropwise under an argon atmosphere to the compound of Example 13 (91 mg, 0.30 mmol) diluted with anhydrous toluene (3 ml). The mixture is brought to 80° C., still under argon, for 2 h 45 min. The crude reaction product is then poured gently into hydrochloric acid solution (0.12 N) at 0° C. The mixture is left stirring for one to two minutes and then poured back immediately into sodium bicarbonate solution at 0° C. until the reaction medium is neutral. The organic phase is then extracted with ether and thereafter five times with dichloromethane, and lastly dried over magnesium sulfate. After evaporation of the solvents under reduced pressure, the hydroxyamide obtained (90 mg, 0.28 mmol) is used directly in the next stage of the reaction.

MS (CI) (isobutane): m/z 319 ([M+H]$^+$, 100), 216 ([M—CH$_2$CON(Me)OMe]$^+$, 10)

Stage B: (1S,2"S)-2-[1-Methyl-6-benzoylmethyl)-1,2,3,6-tetrahydro-2-pyridyl)-1-phenyl ethanol 0.28 mmol of the hydroxyamide obtained in Stage A are placed in anhydrous tetrahydrofuran (3 ml) cooled to −78° C. under an argon atmosphere and with magnetic stirring. Phenyllithium, 1.6 M commercial solution in a cyclohexane/ether mixture (5 eq, 0.88 ml, 1.41 mmol), is added dropwise. When the addition is complete, the temperature is allowed to rise to 25° C. and stirring is then maintained at this temperature overnight. The reaction mixture is poured into saturated ammonium chloride solution at 0° C. The organic phase is extracted a first time with ether and then with dichloromethane, and lastly dried over magnesium sulfate. The crude dehydrolobeline product is converted directly to its hydrochloride by treatment with methanolic hydrogen chloride. The mixture is evaporated, taken up in a minimum of methanol and washed three times with heptane. The salt is then rapidly filtered through silica, eluted with methanol/dichloromethane (0, 0.5, 1 and 2%). Dehydrolobeline hydrochloride is thus isolated without any further method of purification. Treatment of the hydrochloride in a basic medium yields the inseparable mixture of diastereoisomers in the proportions 85:15 (determined by integration of the protons in MNR).

(EI): m/z 335 (M$^{+\cdot}$, 10), 230 (M$^{+\cdot}$-$^\cdot$COPh], 21), 216 ([M$^{+\cdot}$-$^\cdot$CH$_2$COPh], 100), 105 (PhCO$^+$, 57), 94 (PhOH$^{+\cdot}$, 99)

EXAMPLE 16

(2"S)-2,6-Bis(benzoylmethyl)-1-methyl-1,2,3,6-tetrahydropyridine

The procedure is as in Stage E of Example 1, starting from the compound of Example 15.

EXAMPLE 17

(1R,2"S)-1-(1-Methyl-6-benzoylmethyl)-1,2,3,6-tetrahydro-2-pyridyl)-2-propanol

The procedure is as for Example 15, starting from the compound of Example 14.

EXAMPLE 18

(2"S)-2-Acetylmethyl-6-benzoylmethyl-1-methyl-1,2,3,6-tetrahydropyridine

The procedure is as in Stage E of Example 1, starting from the compound of Example 17.

EXAMPLE 19

(1S,2"S,6"R)-2-[1-Methyl-6-(1,1-ethylene dioxy-2-phenethyl)-1,2,3,6-tetrahydro-2-pyridyl]-1-phenylethanol Benzene (5 ml), a large excess of ethylene glycol (1 ml) and para-toluenesulfonic acid (1.2 eq, 27 mg, 0.143 mmol) are placed in a small round-bottomed flask. The mixture is brought to reflux in a Dean-and-Stark apparatus for approximately 10 minutes in order to remove all trace of water. The compound of Example 15 in base form (40 mg, 0.119 mmol), diluted in a few milliliters of benzene, is then added. After 4 hours under reflux in the Dean-and-Stark apparatus, the cooled reaction medium is poured into sodium bicarbonate solution. The organic phase is extracted a first time with ether and then with dichloromethane, and lastly dried over magnesium sulfate. After evaporation of the solvents under reduced pressure the acetal is rapidly filtered through alumina, eluted with dichloromethane and isolated.

Yellow oil

MS (EI): m/z 379 ($M^{+\cdot}$, 10), 258 ($[M^{+\cdot}-{}^{\cdot}CH_2CH(OH)Ph]$, 61), 216 ($[M^{+\cdot}-CH_2C(OCH_2)Ph]$, 100), 149 ($PhC(OCH_2)_2^+$, 99)

EXAMPLE 20

(2"S, 6"R)-2-Benzoylmethyl-1-methyl-6-(1,1-ethylenedioxy-2-phenethyl)-1,2,3,6-tetrahydropyridine The procedure is as in Stage E of Example 1, starting from the compound of Example 19.

PHARMACOLOGICAL STUDY

EXAMPLE A

Study of the capacity of the compounds of the invention to bind to nicotic [sic] receptors The compounds of the present invention were studied, as a first objective, for their capacities to bind to nicotinic receptors using the method of Marks et al. (J. Pharmacol. Exp. Ther., 1986, 30, 427–436). They showed an advantageous affinity for the α7 receptor using as radioligand [$^{125}$I]-α-bungargotoxin. This activity was confirmed in the technique of *Xenopus oocytes* injected with mRNA specific for the α7 receptors.

EXAMPLE B

Passive avoidance test in rats

A study of the memory-facilitating properties was carried out using the passive avoidance test in rats during experimental amnesia by cholinergic blockade.

This test was performed using a two-compartment box, with an unlit black compartment and a white compartment well lit by a 25 W lamp. The two compartments are separated by a drop-down door, and the floor of the black compartment enables an electric shock to be delivered (0.5 mA for 3 seconds). During the learning phase, the animal is placed in the white compartment and the separating door is opened after 60 seconds. After the animal has entered the dark compartment, the door is closed and the animal receives an electric shock. During the rememorization phase 24 hours later, the animal is placed again in the white compartment. Under these conditions, a normal rat no longer goes back into the dark area since it remembers the aversive electric shock. The maximum time of measurement of latency of entry is fixed at 300 seconds. During amnesia induced by cholinergic blockade, the animal again enters the punished compartment.

During treatment with lobeline or with the compounds of the invention, the rats were protected from the experimental amnesia and hence did not go back into the punished compartment, thus testifying the integrity of the functions of recent-fact memory.

EXAMPLE C

Pharmaceutical composition

Preparation formula for 1000 tablets containing a 10 mg dose of the compound of Example 15:

(1S,2"S)-2-(1-Methyl-6-benzoylmethyl-1,2,3,6-tetrahydro-2-pyridyl)-

| | |
|---|---|
| 1-phenylethanol | 10 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

What is claimed is:

1. A compound selected from those of formula (I):

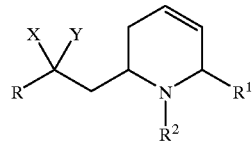

(I)

in which:

X represents a hydrogen atom,

Y represents a hydroxyl group, or X and Y together form an oxo group,

R represents a linear or branched ($C_1$–$C_6$) alkyl group or a phenyl group optionally substituted with one or more halogen atoms or one or more linear or branched ($C_1$–$C_6$) alkyl, ($C_1$–$C_6$) alkoxy, linear or branched ($C_1$–$C_6$) polyhaloalkyl, or hydroxyl groups, $R^1$ represents a hydrogen atom or a group of formula (II):

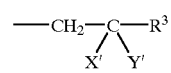

(II)

in which:

X' represents a hydrogen atom,

Y' represents a hydroxyl group, or X' and Y' each simultaneously represent a linear or branched ($C_1$–$C_6$) alkoxy group, or X' and Y' together form an oxo group, $R^3$ represents a linear or branched ($C_1$–$C_6$) alkoxy group or a phenyl group optionally substituted with one or more halogen atoms or one or more linear or branched ($C_1$–$C_6$) alkyl, ($C_1$–$C_6$) alkoxy, linear or branched ($C_1$–$C_6$) polyhaloalkyl or hydroxyl groups, $R^2$ represents a hydrogen atom or a linear or branched ($C_1$–$C_6$) alkyl group optionally substituted with one or more, identical or different, optionally substituted aryl, linear or branched ($C_1$–$C_6$) alkoxy, or hydroxyl groups, on the understanding that, when R and $R^2$ simultaneously represent a methyl group, X represents a hydrogen atom, Y represents a hydroxyl group and $R^1$ represents a group of formula (II) in which X' represents a hydrogen atom and $Y^1$ a hydroxyl group, then $R^3$ cannot represent a phenyl group, its isomers as well as its addition salts with a pharmaceutically acceptable acid or base.

2. A compound of claim 1, for which X represents a hydrogen atom and Y a hydroxyl group.

3. A compound of claim 2 for which $R^1$ represents a group of formula (II):

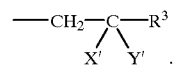

(II)

4. The compound of formula (I) as claimed in claim 1 which is (1S,2"S)-2-(1-methyl-6-benzoylmethyl-1,2,3,6-tetrahydro-2-pyridyl)-1-phenylethanol.

5. A pharmaceutical composition containing at least one compound of claim 1 in combination with one or more pharmaceutically-acceptable, inert, non-excipients or vehicles.

6. A method for the treatment of memory defects associated with cerebral aging and with neurodegenerative diseases including Alzheimer's disease, Parkinson's disease, Pick's disease, Korsakoff's disease and frontal and subcortical dementias, which comprises the step of administering to a patient in need thereof an effective amount of a compound of claim 1.

* * * * *

UNITED STATES PATENT AND TRADEMARK OFFICE
CERTIFICATE OF CORRECTION

PATENT NO. : 6,232,319 B1
DATED : May 15, 2001
INVENTOR(S) : Christian Marazano, et al.

It is certified that error appears in the above-identified patent and that said Letters Patent is hereby corrected as shown below:

<u>Column 18,</u>
Line 12, delete ", inert, non-" after the word acceptable

Signed and Sealed this

Thirteenth Day of November, 2001

*Attest:*

NICHOLAS P. GODICI
*Acting Director of the United States Patent and Trademark Office*

*Attesting Officer*